United States Patent
Sakai et al.

(10) Patent No.: US 6,931,929 B2
(45) Date of Patent: Aug. 23, 2005

(54) FILLER DETECTION METHOD AND FILLER DETECTION DEVICE

(75) Inventors: Takashi Sakai, Tokyo (JP); Minoru Kaneko, Tokyo (JP)

(73) Assignee: Akebono Brake Industry Co., Ltd., Tokyo (JP)

( * ) Notice: Subject to any disclaimer, the term of this patent is extended or adjusted under 35 U.S.C. 154(b) by 2 days.

(21) Appl. No.: 10/408,656

(22) Filed: Apr. 8, 2003

(65) Prior Publication Data

US 2004/0031327 A1 Feb. 19, 2004

(30) Foreign Application Priority Data

Apr. 10, 2002 (JP) ...................................... 2002-107938

(51) Int. Cl.⁷ .......................... G01N 29/12; G01F 23/22
(52) U.S. Cl. .......................... 73/579; 73/594; 73/290 V
(58) Field of Search .......................... 73/579, 582, 588, 73/594, 19.08, 54.03, 803, 290 V, 209 R, 291

(56) References Cited

U.S. PATENT DOCUMENTS

| | | | | |
|---|---|---|---|---|
| 3,641,811 A | * | 2/1972 | Gnaedinger et al. | 73/594 |
| 4,540,981 A | * | 9/1985 | Lapetina et al. | 340/618 |
| 4,654,554 A | * | 3/1987 | Kishi | 381/190 |
| 4,918,988 A | * | 4/1990 | Ebihara et al. | 73/594 |
| 4,991,433 A | * | 2/1991 | Warnaka et al. | 73/290 V |
| 5,717,383 A | * | 2/1998 | Dreyer et al. | 340/621 |
| 5,966,983 A | * | 10/1999 | Pfeiffer et al. | 73/291 |
| 6,138,507 A | * | 10/2000 | Getman et al. | 73/290 V |
| 6,443,004 B1 | * | 9/2002 | Heuft et al. | 73/290 V |
| 6,587,567 B1 | * | 7/2003 | Yamamoto | 381/190 |
| 6,653,762 B2 | * | 11/2003 | Takeshima | 310/340 |

FOREIGN PATENT DOCUMENTS

| | | | |
|---|---|---|---|
| DE | 19905926 | * | 8/2000 |
| JP | 7-269120 | | 10/1995 |
| JP | 7-33303 | * | 12/1995 |
| JP | 10-197467 | | 7/1998 |
| JP | 2836799-82 | | 10/1998 |
| JP | 2001-4438 | * | 1/2001 |
| JP | 2003-194615 | * | 7/2003 |

* cited by examiner

*Primary Examiner*—Helen Kwok
(74) *Attorney, Agent, or Firm*—Morgan, Lewis & Bockius LLP

(57) ABSTRACT

A sine wave electric signal whose frequency continuously varies within a predetermined frequency range is applied to a piezoelectric speaker, whereby a vibration frequency characteristic of the piezoelectric speaker is detected. A change of the frequency characteristic of the piezoelectric speaker when the piezoelectric speaker is brought into contact with concrete filled into a precast concrete form is detected based on the vibration frequency characteristic detected. With this unique feature, a filling status of concrete in the precast concrete form can exactly be detected independently of the hardness of water contained in the concrete and ambient temperature, and even if a temperature difference between air and the concrete is small.

6 Claims, 5 Drawing Sheets

FILLER DETECTION METHOD AND FILLER DETECTION DEVICE

BACKGROUND OF THE INVENTION

The present invention relates to a filler detection method and a filler detection device which each detect a filling status of a concrete filled to a form formed with a precast concrete, for example.

In a structure of a building, by convention, reinforcing bars are arranged in a form formed with precast concrete (referred to as a "precast concrete form"), and concrete is filled or poured into the precast concrete form.

Recently, with the trend of design diversification, the precast concrete form is also complicated in shape. In this situation, the market needs a technical method which is capable of non-destructively inspecting if concrete satisfactorily reaches the distal regions of the complicatedly shaped form.

Examples of such non-destructive inspection methods, currently commercialized, are JP-A-07-269120 (Japanese Application Publication Number: Hei07-269120), JP-A-10-197467 (Japanese Application Publication Number: Hei10-197467) and JP-B2-2836799, (Japanese Patent Registration Number: 2836799). In each of those technical methods, two electrodes are disposed within the precast concrete form. When concrete contacts with those two electrodes, an electric potential appears between those electrodes. The filling of concrete is detected on the basis of the detected electric potential.

In addition to those three methods, another technique exists. In the technique, a thermocouple is located in the precast concrete form. A status of the filling of concrete is detected based on a temperature variation by the utilization of a difference between the specific heat of air and that of concrete.

Those conventional concrete filler detection methods have the following problems.

In the technique in which the electrodes are located within the precast concrete form, an electric potential between the electrodes is affected by the hardness of water contained in the concrete and ambient temperature, and is not fixed in value. Accordingly, it is necessary to set up a reference value of the electric potential in a building site each and every time. In this respect, the working efficiency is not good.

The conventional technique, which detects a filling status of concrete by utilizing the specific heat difference between air and concrete, cannot detect accurately the concrete filling status when a temperature difference between the concrete and air is small. Particularly, in the case of a building structure built in the sea, the interior of it is filled with seawater. Therefore, it is difficult to detect the filling status based on the temperature difference.

Any of the conventional techniques cannot distinguish between mortar and concrete containing the aggregate. Because, the filling status detecting systems, currently commercialized, are both designed to detect the filling status by utilizing chemical properties of the mortar, and the concrete is different from the mortar in that the former contains the aggregate, and hence, if the system cannot recognize the presence of the aggregate, it cannot distinguish between the concrete and the mortar.

SUMMARY OF THE INVENTION

Accordingly, an object of the present invention is to provide a filler detection method and a filler detection device which are each capable of accurately and easily detecting a filling status of a filler, e.g., a concrete, placed in such a predetermined space that it is almost impossible to check the filler contained therein by the eye, even if the space is a closed space or an open space.

According to the present invention, there is provided a filler detection method comprising the steps of: applying an electric signal whose frequency varies within a predetermined frequency range with respect to time to a sensor element for converting electric energy into mechanical energy; detecting a change of a vibration frequency characteristic of the sensor element when the sensor element is brought into contact with contact with a filler filled to a predetermined space; and detecting a filling status of the filler in the space based on the detected change of the vibration frequency characteristic of the sensor element.

This method detects a filling status of the filler filled to the space by utilizing a fact that a frequency characteristic of the sensor element when the filler is brought into contact with the sensor element is different from that of the sensor element when it is not brought into contact with the sensor element. Therefore, a filling status of the filler can exactly be detected independently of a change of ambient temperature. When the filler is concrete, for example, a filling status of the concrete can exactly be detected independently of ambient temperature, concrete temperature, the hardness of water used, and the like.

The natural vibration frequency characteristic of the sensor element is already known. Accordingly, there is no need of any special work of setting up the reference value in a building site, and hence, the filling status of the filler may be detected for a short time. The vibration frequency characteristic of the sensor element varies depending on a specific gravity and a viscosity of a material in contact with the sensor element. Therefore, by measuring a change of each of those properties, it is easy to decide whether the filler is gas, liquid or solid.

According to another aspect of the invention, there is provided a filler detection method comprising the steps of: applying an electric signal whose frequency varies within a predetermined frequency range with respect to time to a plurality of sensor elements, each separately disposed, each for converting electric energy into mechanical energy; detecting a change of a vibration frequency characteristic of each sensor element when each sensor element is brought into contact with contact with a filler filled to a predetermined space; and detecting a filling status of a composition constituting the filler.

In this method, an electric signal is applied to those sensor elements, and changes of the vibration frequency characteristics of those sensor elements are detected. Therefore, filling statuses of compositions of the filler are detected. When the filler is concrete, for example, the compositions are mortar and a aggregate. A change of the vibration frequency characteristic of the sensor element when it contacts with the mortar is different from the corresponding one when it contacts with the aggregate. In this case, if the aggregate is not detected, it is recognized that the concrete was not filled correctly into the form.

According to still another aspect, there is provided a filler detection device comprising: a sensor element for converting electric energy into mechanical energy; signal generating/applying means for repeatedly generating an electric signal whose frequency varies within a predetermined frequency range with respect to time, and for applying the generated electric signal to the sensor element; and frequency characteristic detecting means for detecting a vibration frequency characteristic of the sensor element by applying the electric signal generated by the signal generating/applying means to the sensor element.

In the filler detection device thus constructed, a sensor element (e.g., a piezoelectric speaker) for converting electric energy into mechanical energy is vibrated by a sine wave signal. And a vibration frequency characteristic of the sensor element is detected by varying the frequency of the sine wave signal within an optional frequency range. Accordingly, it is possible to detect a filling status of the filler in a space by a change of the vibration frequency characteristic of the sensor element when it contacts with the filler, such as concrete.

The filler detection device further comprises judging means for judging whether or not an object to be detected in a predetermined space contacts with the sensor element, by using, as a reference, a signal output from the frequency characteristic detecting means when nothing contacts with the sensor element.

In the filler detection device, it is easy to judge whether or not the filler, e.g., concrete, contacts with the sensor element, from the output signal of the judging part.

According to a further aspect of the invention, there is provided a filler detection device comprising: a plurality of sensor elements each for converting electric energy into mechanical energy; signal generating/applying means for repeatedly generating an electric signal whose frequency varies within a predetermined frequency range with respect to time, and for applying the generated electric signal to the plurality of sensor elements; frequency characteristic detecting means for detecting a vibration frequency characteristic of each sensor element by applying the electric signal generated by the signal generating/applying means to each sensor element; and judging means for judging a filling status of a composition constituting a filler by detecting a change of a vibration frequency characteristic of each sensor element when each sensor element is brought into contact with contact with the filler filled to a predetermined space, by using, as a reference, a signal output from each frequency characteristic detecting means when nothing contacts with each sensor element.

In this method, an electric signal is applied to those sensor elements, and changes of the vibration frequency characteristics of those sensor elements are detected. Therefore, filling statuses of compositions of the filler are detected. When the filler is concrete, for example, the compositions are mortar and an aggregate. A change of the vibration frequency characteristic of the sensor element when it contacts with the mortar is different from the corresponding one when it contacts with the aggregate. In this case, if the aggregate is not detected, it is recognized that the concrete was not filled correctly into the form.

In those filler detection devices, the sensor element is a piezoelectric speaker.

Since the piezoelectric speaker is used for the sensor element, the filler detection device may be realized at low cost.

DETAILED DESCRIPTION OF THE PREFERRED EMBODIMENTS

The preferred embodiment of the present invention will be described with reference to the accompanying drawings.

Figure 1:
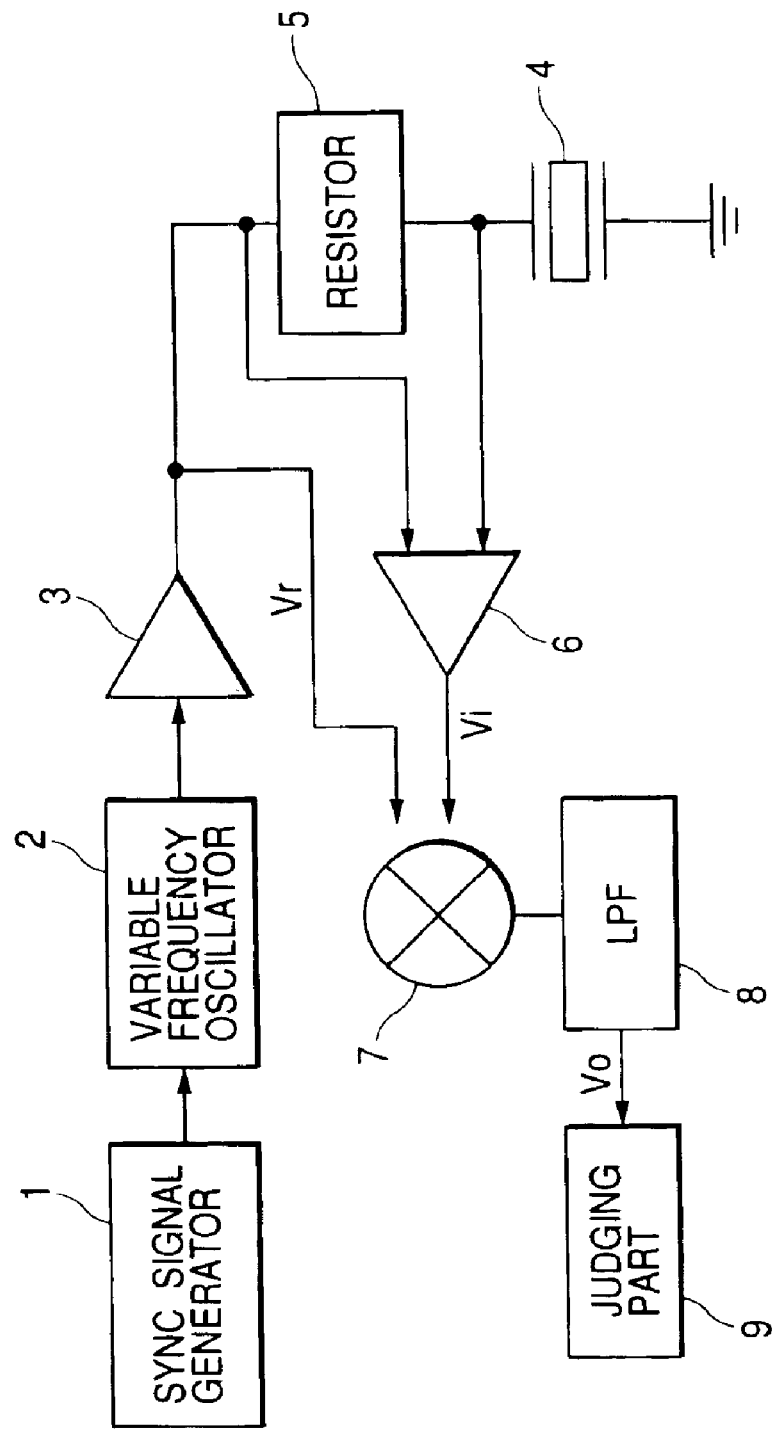
FIG. 1 is a block diagram showing a filler detection device which is an embodiment of the invention.

FIG. 1 is a block diagram showing a filler detection device which is an embodiment of the invention.

In the figure, the filler detection device of the embodiment is made up of a sync signal generator 1, a variable frequency oscillator 2, an amplifier 3, a piezoelectric speaker (sensor element) 4, a resistor 5, a differential amplifier 6, a 4-quadrant multiplier 7, a low pass filter (LPF) 8, and a judging part 9.

The sync signal generator 1 generates a sync signal for repeatedly operating the variable frequency oscillator 2. The variable frequency oscillator 2 generates a sine-wave electric signal the frequency of which continuously varies within a predetermined frequency range (for example, 1 kHz to 20 kHz). In this case, every time the sync signal generator 1 produces a sync signal, the variable frequency oscillator repeatedly generates a sine wave signal and its frequency varies from an initial frequency (e.g., 1 kHz) thereof successively. The amplifier 3 receives the sine wave signal from the variable frequency oscillator 2, and amplifies it to have a signal level high enough to drive the piezoelectric speaker 4, and outputs the resultant as a vibration signal Vr. In the embodiment, the sync signal generator 1, the variable frequency oscillator 2 and the amplifier 3 will be referred to collectively as "signal generating/applying means".

The piezoelectric speaker 4 uses a piezoelectric element, and converts an electric signal into a mechanical signal, and outputs the converted one. The resistor 5 is inserted in series between the amplifier 3 and the piezoelectric speaker 4, and a voltage corresponding to a current flowing through the piezoelectric speaker 4 appears across the resistor. The current flowing through the piezoelectric speaker 4 varies with a variation the frequency. Therefore, the voltage across the resistor 5 reflects a frequency characteristic of the piezoelectric speaker 4.

The differential amplifier 6 amplifies the voltage across the resistor 5 and outputs the resultant in the form of a voltage Vi. The piezoelectric speaker 4 multiplies the vibration signal Vr by the voltage Vi to thereby remove noise components from those signals. The low pass filter 8 removes a signal component of cos(2 wt+a+b) (to be described later) from the output signal of the 4-quadrant multiplier 7, and outputs the resultant signal (output signal Vo). In the embodiment, the resistor 5, the differential amplifier 6, the 4-quadrant multiplier 7 and the low pass filter 8 will be referred to collectively as "frequency characteristic detecting means".

The judging part 9 includes a microcomputer and a display device, such as an LCD (liquid crystal display). The judging part judges whether or not concrete in the precast concrete form is in contact with the piezoelectric speaker 4, from a signal output form the low pass filter 8, while using, as a reference, a natural vibration frequency characteristic of the piezoelectric speaker when the concrete is not in contact with the piezoelectric speaker 4. And, the judging part displays the judging result (good or no good) on the display device. In this case, if the natural vibration frequency characteristic of the piezoelectric speaker 4 is once set, there is no need of setting it in subsequent stages, except the maintenance of the device. The natural vibration frequency characteristic of the piezoelectric speaker 4 is stored into a memory of the microcomputer.

With such an arrangement, a sine wave signal generated by the variable frequency oscillator 2 is amplified by the amplifier 3, and is input as the vibration signal Vr to the piezoelectric speaker 4, and the vibration signal causes the piezoelectric speaker 4 to mechanically vibrate. The vibration signal Vr is input also to the 4-quadrant multiplier 7. When the piezoelectric speaker 4 mechanically vibrates, a voltage appears across the resistor 5, which the voltage corresponds to a current flowing through the piezoelectric speaker 4. This voltage is amplified by the differential amplifier 6, and output as the voltage Vi. The voltage Vi and the vibration signal Vr from the amplifier 3 are multiplied by the 4-quadrant multiplier 7. The output signal of the 4-quadrant multiplier is applied to the low pass filter 8, which in turn removes the cos(2 wt+a+b) component from the output signal, and outputs the resultant as an output signal Vo.

Figure 2:
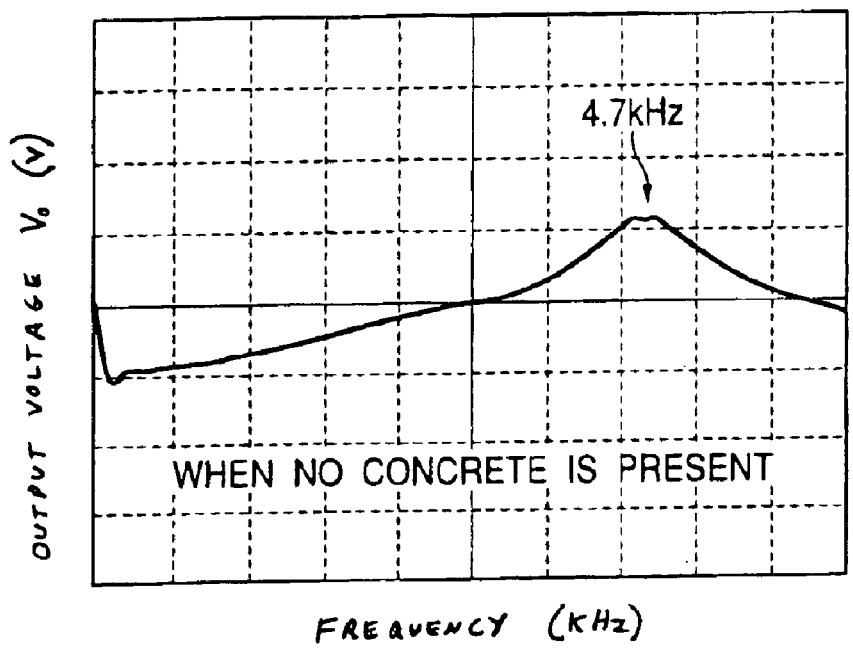
FIG. 2 is a graph showing a measuring result by the filler detection device of FIG. 1, viz., a voltage waveform output from the filler detection device when no concrete is present in the precast concrete form.
Figure 3:
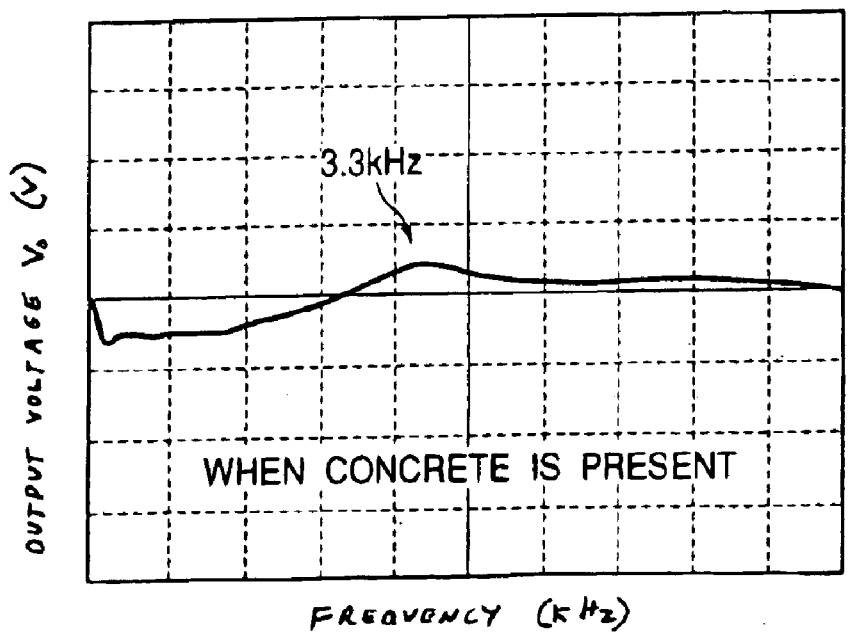
FIG. 3 is a graph showing a measuring result by the filler detection device of FIG. 1, viz., a voltage waveform output from the filler detection device when concrete is present in the precast concrete form.

The output signal Vo reflects the frequency characteristic (amplitude and phase) of the piezoelectric speaker 4 with respect to a frequency variation of the vibration signal. When nothing is in contact with the surface of the piezoelectric speaker 4, a voltage appears as shown in FIG. 2. The voltage has a peak value appears at a frequency near the natural vibration frequency of the piezoelectric speaker 4. When concrete is placed around the piezoelectric speaker 4, the vibration characteristic of the piezoelectric speaker 4 varies, and a position and an amplitude of the peak voltage greatly vary as shown in FIG. 3. The judging part 9 judges a filling status of the concrete from the change of the peak voltage, and displays the judging result on the display device. In this way, the filling status of the concrete is easily judged.

The operation principle of the filler detection device may mathematically be described in the following manner.

It is assumed that Vr=A sin(wt+a) and Vi=B sin(wt+b), where A and B are amplitudes of the voltages, and w is a frequency, and a and b are phase shifts.

$$Vr \times Vi = A\sin(wt+a) \times B\sin(wt+b) \quad (1)$$
$$= AB[\cos(b-a) - \cos(2wt+a+b)]/2$$

In the equation (1), the term cos(b−a) is a DC component varying with a phase difference, and includes an amplitude component of the voltage Vi. The term cos(2 wt+a+b) indicates a signal having a frequency two times as high as that of the original vibration signal Vr and the voltage Vi. Since information on the frequency characteristic as required here is the amplitude (magnitude) of the voltage Vi, then only the term cos(b−a) in the equation (1) is required. Therefore, what a designer has to do is to remove the term or component cos(2 wt+a+b) from the output signal of the 4-quadrant multiplier by use of the low pass filter 8. In this way, the frequency characteristic appears in the form of the voltage Vo.

As shown in FIGS. 2 and 3, when concrete is filled into the space, such as the precast concrete form, a frequency and a level of the peak voltage change, and hence, a filling status of the concrete can be obtained from their changes.

In this way, in the embodiment, an electric signal of which the frequency varies within a predetermined frequency range with respect to time is generated. The electric signal is applied to the piezoelectric speaker 4 and a vibration frequency characteristic of the piezoelectric speaker is detected. The piezoelectric speaker is brought into contact with the concrete filled in the precast concrete form, and in this state, the vibration frequency characteristic of the piezoelectric speaker 4 is measured. A change of this vibration frequency characteristic from that detected vibration frequency characteristic is detected. As a result, a filling status of concrete in the precast concrete form can be detected independently of ambient temperature, concrete temperature, the hardness of water used, and the like. Thus, the filler detection device can exactly and easily detect the filling status of concrete in the precast concrete form.

In the case of general concrete, mortar (consisting of cement, sand and water) and coarse aggregates are sufficiently agitated by a concrete mixer, and then the resultant is poured into the precast concrete form. However, there is a case where the reinforcements are overcrowded, and the coarse aggregates are caught by the reinforcing bars, and only the mortar is poured into the precast concrete form. In this case, a strength of the concrete is possibly insufficient. Accordingly, it is desired to develop a method capable of reliably checking if the coarse aggregate is present.

Figure 4:
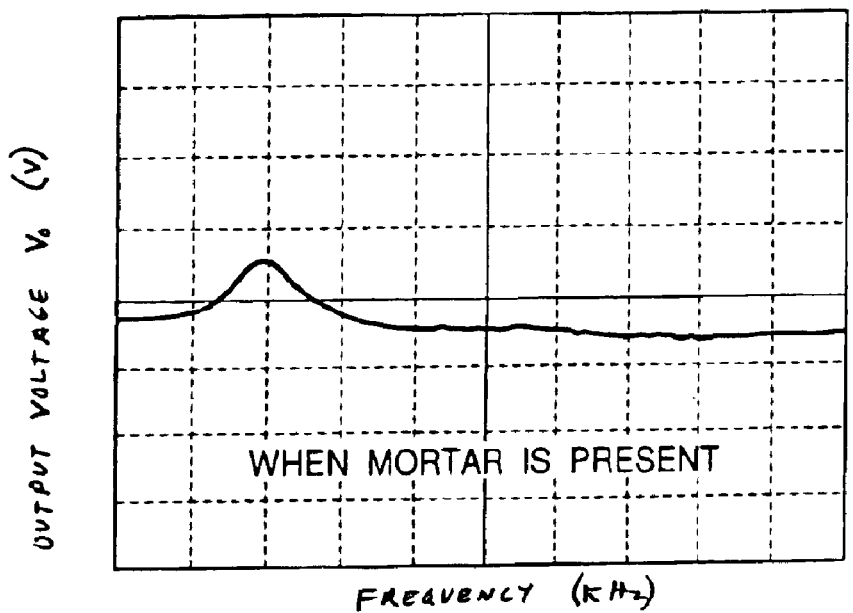
FIG. 4 is a graph showing a measuring result by the filler detection device of FIG. 1, viz., a voltage waveform output from the filler detection device when mortar is present in the precast concrete form.

When the coarse aggregate contacts with the piezoelectric speaker 4 as the sensor element, a waveform of the output voltage is substantially flat while having a negligible peak amplitude, as shown in FIG. 3. When the piezoelectric speaker contacts with mortar containing no coarse aggregate, the output voltage has a waveform as shown in FIG. 4. As shown, a peak voltage appears at a position closer to a low frequency region and is low in value.

Figure 5:
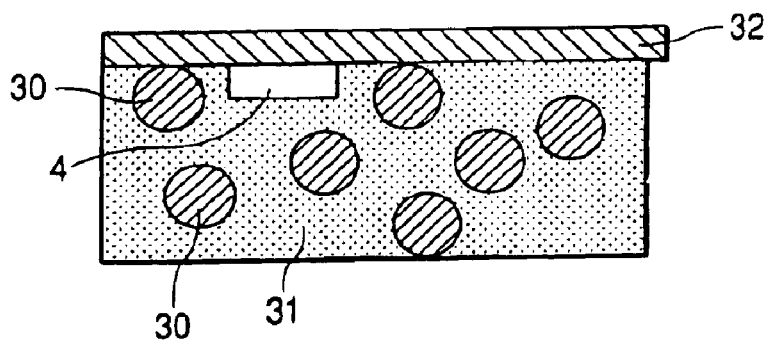
FIG. 5 is a diagram showing a filling status of concrete in a precast concrete form when no aggregate is in contact with a piezoelectric speaker.
Figure 6:
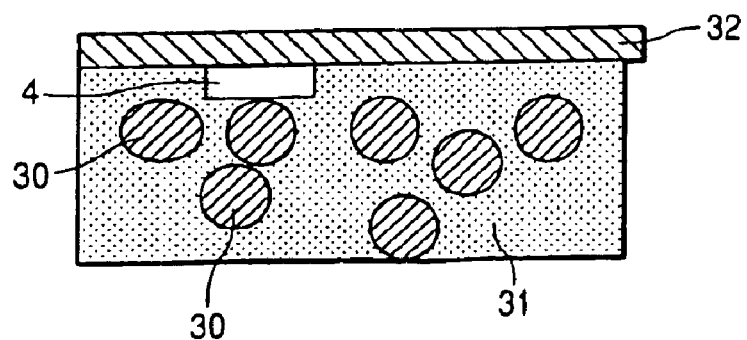
FIG. 6 is a diagram showing a filling status of concrete in a precast concrete form when an aggregate is in contact with a piezoelectric speaker.

The following problem arises when the piezoelectric speaker 4 is reduced in size, and is installed at a place where a filling of concrete is to be detected, and concrete is filled to the precast concrete form. When a coarse aggregate 30 does not contact with the piezoelectric speaker 4 as shown in FIG. 5, the waveform of the output signal is as shown in FIG. 4. Therefore, the filler detection device mistakenly recognizes that the precast concrete form is filled with mortar 31. On the other hand, when a coarse aggregate 30 contacts with the piezoelectric speaker 4 as shown in FIG. 6, the waveform of the output signal is as shown in FIG. 3. Therefore, the filler detection device correctly recognizes that the precast concrete form is filled with concrete. In FIGS. 5 and 6, reference numeral 32 designates a combination panel.

When the piezoelectric speaker 4 per se is increased in size, a chance that it contacts with the coarse aggregate 30 increases. In this case, however, amass of the piezoelectric speaker 4 increases, and hence, the piezoelectric speaker is hard to vibrate, and a sensitivity of the piezoelectric speaker 4 degrades. For this reason, there is a limit in increasing the size of the piezoelectric speaker 4. However, when the size of the piezoelectric speaker 4 is reduced but a number of the piezoelectric speakers is increased, a probability that the piezoelectric speaker will contact with the coarse aggregate 30 increases. Accordingly, a judgement accuracy will be increased. Another embodiment of the invention will be described in which a filling status of the filler is detected by detecting if the coarse aggregate 30 as a composition constituting the concrete is present.

Figure 7:
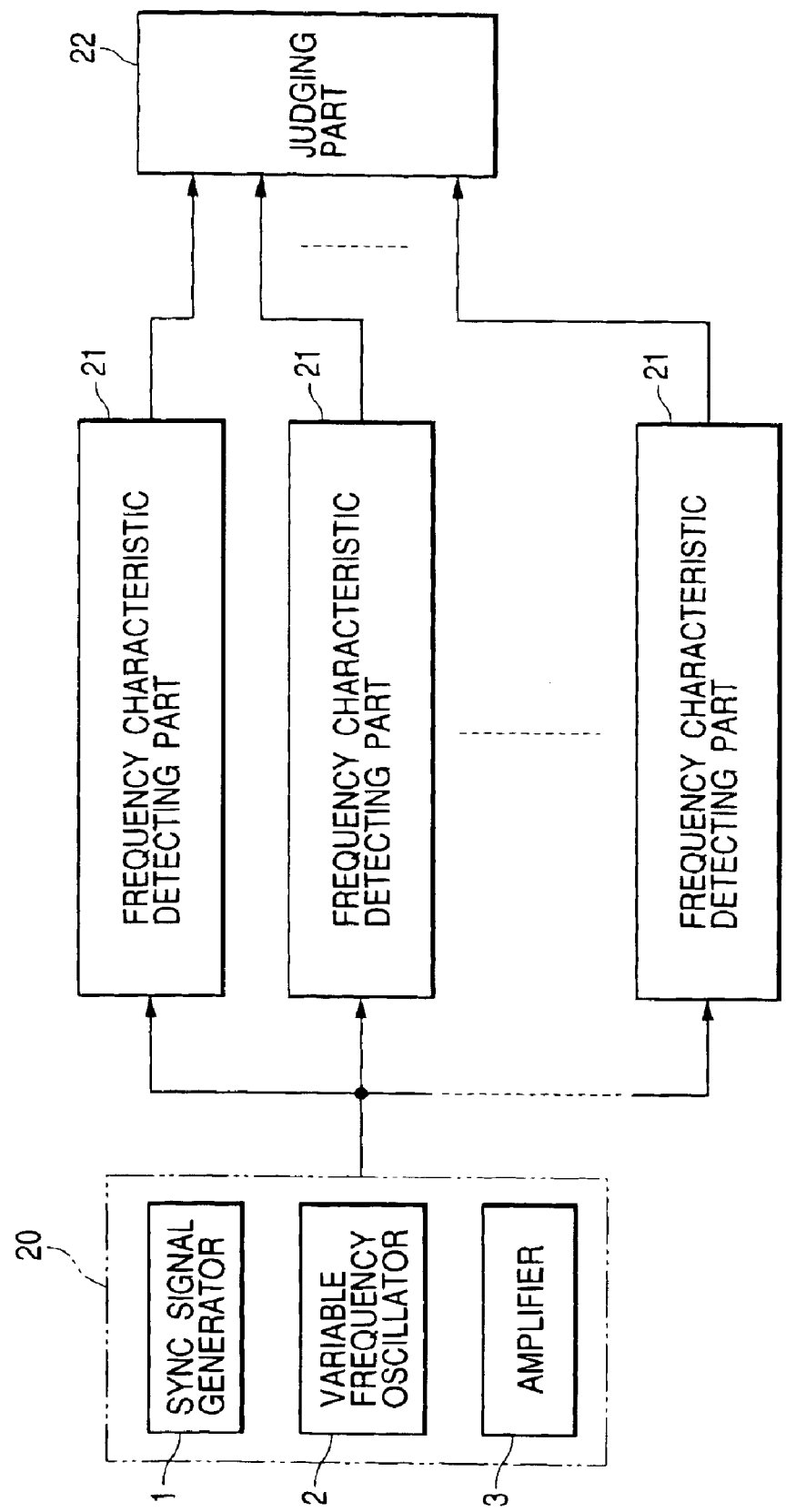
FIG. 7 is a block diagram showing a filler detection device which is another embodiment of the invention.

FIG. 7 is a block diagram showing a filler detection device which is another embodiment of the invention.

The filler detection device of the instant embodiment is made up of a vibration-signal generating/applying part 20, a plurality of frequency characteristic detecting parts 21, and a judging part 22. The vibration-signal generating/applying part 20 contains a sync signal generator 1, a variable frequency oscillator 2 and an amplifier 3, which are the same as those in the filler detection device of the first embodiment. The vibration-signal generating/applying part generates a sine-wave electric signal the frequency of which continuously varies within a predetermined frequency range (for example, 1 kHz to 20 kHz).

Figure 8:
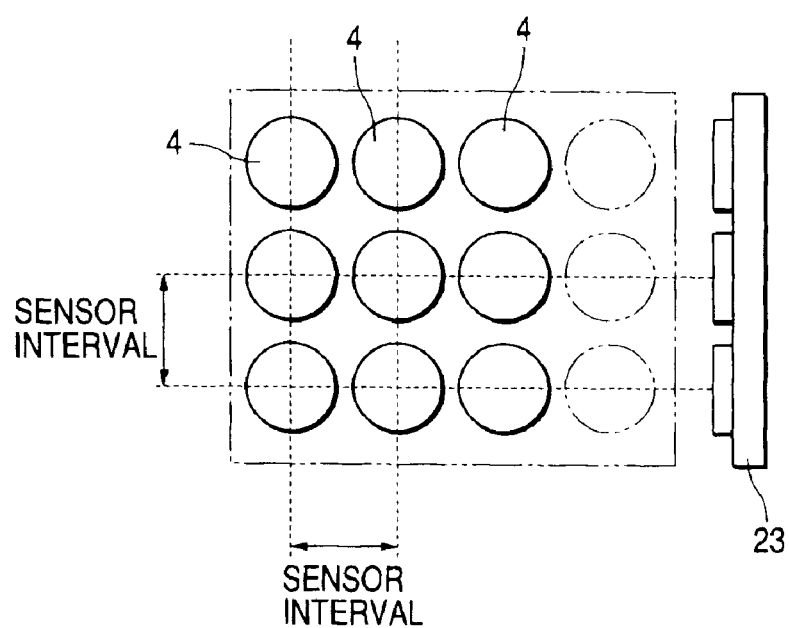
FIG. 8 is a diagram showing a sensor part in the filler detection device of FIG. 7.

Each of those frequency characteristic detecting parts 21 contains a piezoelectric speaker 4, a resistor 5, a differential amplifier 6, a 4-quadrant multiplier 7 and a low pass filter 8, which are the same as those in the embodiment 1, and detects a vibration frequency characteristic of the piezoelectric speaker 4. The judging part 22 detects the mortar and the coarse aggregate as compositions forming the concrete from the detecting result by each frequency characteristic detecting part 21. The piezoelectric speakers 4 in each frequency characteristic detecting part 21 are arrayed at fixed pitches on a plate 23 as shown in FIG. 8. In this instance, a total of nine piezoelectric speakers 4 are arrayed. Those piezoelectric speakers 4 and the plate 23 for fixedly supporting those piezoelectric speakers will be referred to as a "sensor part".

The judging part 22 judges whether the filler is concrete or mortar in the following manner. The frequency characteristics that are output from the frequency characteristic detecting parts 21 when nothing is brought into contact with the sensor part, are used as reference frequency characteristics. Changes of the frequency characteristics that are output from the frequency characteristic detecting parts when the sensor parts are each brought into contact with concrete in the precast concrete form, from the reference ones are detected. When the vibration frequency characteristics of all the piezoelectric speakers 4 in the sensor part are changed as shown in FIG. 4, the judging part judges that the filler is mortar not containing the coarse aggregate. When the vibration frequency characteristic of any of the piezoelectric speakers 4 is changed as shown in FIG. 3, the judging part judges that the filler is concrete. If the judging part judges that the filler of concrete is mortar, it may be considered that the reinforcements are overcrowded, and the coarse aggregates are caught by the reinforcing bars, and only the mortar is poured into the precast concrete form. If the filler is concrete, it may be considered that the judging part correctly judges that the filler is concrete.

Figure 9:
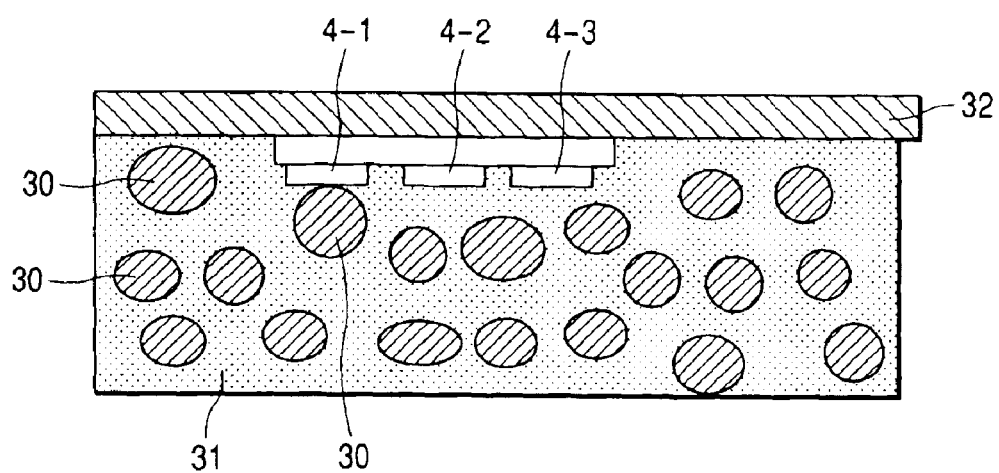
FIG. 9 is a diagram showing a filling status of concrete in a precast concrete form when an aggregate is in contact with one of piezoelectric speakers.

FIG. 9 is a diagram showing a filling status of the filler when the sensor parts are used. As shown, a piezoelectric speaker 4-1 contacts with the coarse aggregate 30. Therefore, it is recognized that the precast concrete form is filed with concrete even if the remaining piezoelectric speakers 4-1, 4-2 do not contact with the coarse aggregate 30. As the number of piezoelectric speakers 4 is larger and the interval of the adjacent piezoelectric speakers is narrower, a probability that the piezoelectric speaker will contact with the coarse aggregate 30 in the concrete, increases, and hence the judgement accuracy increases. Actually, there is a limit in reducing the speaker size. Therefore, it is preferable to select the number of piezoelectric speakers and the speaker pitch in accordance with a ratio of the coarse aggregate to the concrete actually used. A maximum size of the coarse aggregate generally used is 20 or 25 mm, and a percentage of voids (portion not having the coarse aggregate≈mortar+fine aggregate) is generally 30 to 40%. It is preferable to consider those factors in selecting the number of piezoelectric speakers and the speaker size.

Thus, in the embodiment, an electric signal is applied to those piezoelectric speakers 4, and changes of the vibration frequency characteristics of those piezoelectric speakers are detected. Therefore, the filler detection device can detect filling statuses of mortar and aggregate, which are compositions of concrete.

In the embodiments mentioned above, a sine wave signal whose frequency varies within a single frequency range, is used. In an alternative, a frequency range selector (not shown) is provided for selecting one of those frequency ranges, and a desired frequency range of a sine wave signal is selected from those frequency ranges. In this case, the variable frequency oscillator 2 repeatedly generates a sine wave signal whose frequency is varied within a frequency range as selected by the frequency range selector. Thus, with the function capable of selecting a frequency range from the plurality of frequency ranges, an optimum frequency range maybe selected in accordance with the structure of the precast concrete form and physical characteristics of material used. Therefore, more accurate measurement is realized.

The embodiments include the judging parts 9 and 22. However, those judging parts are not essential, but may each be substituted by a waveform measuring instrument, such as an oscilloscope, and a waveform of an output signal of the low pass filter 8 is measured by the instrument. Where the waveform measuring instrument, such as an oscilloscope, is used, the cost to manufacture the filler detection device is reduced by an amount corresponding to the removal of the judging part 9 or 22.

In the embodiments, the invention is applied to the detection of a filling status of concrete filled into a closed space, such as a precast concrete form. It is evident that the invention may be applied to the detection of a filling status of concrete filled into a wooden form or a form formed with steel material.

In a first filler detection method, an electric signal of which the frequency varies within a predetermined frequency range with respect to time is generated. The electric signal is applied to the element for converting electric energy to mechanical energy, and a vibration frequency characteristic of the element is detected. The element is brought into contact with the filler filled in the space, and in this state, the vibration frequency characteristic of the piezoelectric speaker 4 is measured. A filling status of the filler in the space can exactly and easily be detected.

In a second filler detection method, an electric signal is applied to plurality of sensor elements, and changes of the vibration frequency characteristics of those sensor elements are detected. Therefore, filling statuses of compositions of the filler are detected.

In a first filler detection device, a sensor element (e.g., a piezoelectric speaker) for converting electric energy into mechanical energy is vibrated by a sine wave signal. And a vibration frequency characteristic of the sensor element is detected by varying the frequency of the sine wave signal within an optional frequency range. Accordingly, it is possible to detect a filling status of the filler in a space by a change of the vibration frequency characteristic of the sensor element when it contacts with the filler, such as concrete.

In a second filler detection device, it is easy to judge whether or not the filler, e.g., concrete, contacts with the sensor element, from the output signal of the judging part.

In a third filler detection device, an electric signal is applied to a plurality of sensor elements, and changes of the vibration frequency characteristics of those sensor elements are detected. Therefore, filling statuses of compositions of the filler are detected.

In the fourth filler detection device, the piezoelectric speaker is used for the sensor element, the filler detection device may be realized at low cost.

What is claimed is:

1. A filler detection method comprising:

applying an electric signal having a frequency that varies within a predetermined frequency range with respect to time to a sensor element for converting electric energy into mechanical energy;

detecting a change of a vibration frequency characteristic of the sensor element when the sensor element is brought into contact with a filler filled to a predetermined space, the detecting the change of vibration frequency characteristic being simultaneous with the applying the electric signal; and judging a filling status of the filler in the space based on the detected change of the vibration frequency characteristic of the sensor element.

2. A filler detection method comprising:

applying an electric signal having a frequency that varies within a predetermined frequency range with respect to time to a plurality of sensor elements for converting electric energy into mechanical energy, the plurality of sensor elements arrayed at fixed pitch intervals;

detecting a change of a vibration frequency characteristic of each sensor element when each sensor element is brought into contact with a filler filled to a predetermined space, the detecting the change of vibration frequency characteristic being simultaneous with the applying the electric signal; and judging a filling status of a composition constituting the filler based on the detected change of the vibration frequency characteristic of the sensor elements.

3. A filler detection device comprising:

a sensor element for converting electric energy into mechanical energy;

signal generating/applying means for repeatedly generating an electric signal having a frequency that varies within a predetermined frequency range with respect to time, and for applying said generated electric signal to the sensor element; and frequency characteristic detecting means for detecting a vibration frequency characteristic of the sensor element when the sensor element contacts an object to be detected by applying the electric signal generated by the signal generating/applying means to the sensor element simultaneously with detecting the vibration frequency characteristic of the sensor element.

4. The filler detection device according to claim 3, further comprising:

judging means for judging whether or not the object to be detected in a predetermined space contacts the sensor element, by using, as a reference, a signal output from the frequency characteristic detecting means when the object to be detected does not contact said sensor element.

5. A filler detection device comprising:

a plurality of sensor elements each for converting electric energy into mechanical energy;

signal generating/applying means for repeatedly generating an electric signal having a frequency that varies within a predetermined frequency range with respect to time, and for applying said generated electric signal to the plurality of sensor elements;

frequency characteristic detecting means for detecting a vibration frequency characteristic of each sensor element by applying the electric signal generated by the signal generating/applying means to each sensor element simultaneously with detecting the vibration frequency characteristic of each sensor element, and judging means for judging a filling status of a composition constituting a filler by detecting a change of a vibration frequency characteristic of each sensor element when each sensor element is brought into contact with said filler filled to a predetermined space, by using, as a reference, a signal output from each frequency characteristic detecting means when the filler does not contact each said sensor element.

6. The filler detection device according to any one of claims 3 to 5, wherein said sensor element is a piezoelectric speaker.

* * * * *